(12) United States Patent
Miklos et al.

(10) Patent No.: US 8,359,903 B2
(45) Date of Patent: Jan. 29, 2013

(54) PHOTOACOUSTIC DETECTOR WITH TWO BEAM PATHS FOR EXCITATION LIGHT

(75) Inventors: Andras Miklos, Stuttgart (DE); Judit Angster, Stuttgart (DE)

(73) Assignee: Fraunhofer-Gesellschaft zur Foerderung der Angewandten Forschung E.V., Munich (DE)

(*) Notice: Subject to any disclaimer, the term of this patent is extended or adjusted under 35 U.S.C. 154(b) by 428 days.

(21) Appl. No.: 12/593,154

(22) PCT Filed: Mar. 27, 2008

(86) PCT No.: PCT/EP2008/002430
§ 371 (c)(1),
(2), (4) Date: Sep. 25, 2009

(87) PCT Pub. No.: WO2008/116654
PCT Pub. Date: Oct. 2, 2008

(65) Prior Publication Data
US 2010/0101305 A1    Apr. 29, 2010

(30) Foreign Application Priority Data
Mar. 27, 2007  (DE) .......................... 10 2007 014 520

(51) Int. Cl.
*G01N 21/85* (2006.01)
*G01N 29/036* (2006.01)

(52) U.S. Cl. ................. 73/24.02; 73/24.06; 250/339.07; 356/336; 356/438; 356/440

(58) Field of Classification Search .................... 73/643, 73/579, 24.02, 24.06; 250/339.07; 356/438, 356/440, 336
See application file for complete search history.

(56) References Cited

U.S. PATENT DOCUMENTS 3,970,387 A * 7/1976 Faulhaber et al. ............... 356/51
3,995,960 A * 12/1976 Fletcher et al. ............... 356/433
(Continued)

FOREIGN PATENT DOCUMENTS
DE    24 05 317    10/1975
DE    28 49 379    5/1979
(Continued)

OTHER PUBLICATIONS

International Search Report in Application No. PCT/EP2008/002430 and the English-language International Search Report.
(Continued)

*Primary Examiner* — Peter Macchiarolo
*Assistant Examiner* — Rose M Miller
(74) *Attorney, Agent, or Firm* — Greenblum & Bernstein, P.L.C.

(57) ABSTRACT

A photoacoustic detector for providing a measurement, includes a first light source and a second light source each configured to provide light of a same intensity while retaining a same spectral distribution. Additionally, the photoacoustic detector includes a first beam path allocated to the first light source and at least one second beam path allocated to the second light source, wherein a different absorption of light occurs in the first path and the second beam path in at least one selected wavelength range. Further, the photoacoustic detector includes a photoacoustic measuring cell; and a mechanism for alternately guiding light from the first beam path and from the second beam path into the photoacoustic measuring cell. When alternately guiding light from the first beam path and from the second beam path into the photoacoustic measuring cell, the same intensity of the first light source and the second light source prevents generation of a photoacoustic signal due to light source intensity variation that distorts the measurement.

15 Claims, 3 Drawing Sheets

U.S. PATENT DOCUMENTS

| | | | |
|---|---|---|---|
| 4,269,509 A * | 5/1981 | Berry et al. | 356/301 |
| 4,682,031 A | 7/1987 | Fabinski et al. | |
| 4,817,413 A * | 4/1989 | Asano et al. | 73/24.02 |
| 5,933,245 A | 8/1999 | Wood et al. | |
| 6,006,585 A | 12/1999 | Forster | |
| 2006/0254340 A1 | 11/2006 | Baraket et al. | |
| 2006/0290944 A1 * | 12/2006 | Arnott et al. | 356/519 |

FOREIGN PATENT DOCUMENTS

| | | |
|---|---|---|
| DE | 10 2005 025675 | 11/2006 |
| EP | 0199365 | 10/1986 |
| EP | 0855592 | 7/1998 |
| GB | 2358245 | 7/2001 |
| WO | WO 2005/093390 | 10/2005 |

OTHER PUBLICATIONS

German Search Report and accompanying German Office Action dated Oct. 16, 2007 with partial English language translation.

* cited by examiner

PHOTOACOUSTIC DETECTOR WITH TWO BEAM PATHS FOR EXCITATION LIGHT

CROSS REFERENCE TO RELATED APPLICATIONS

The present application is a U.S. National Stage of International Application No. PCT/EP2008/002430 filed Mar. 27, 2008, which published as WO 2008/116654 A1 on Oct. 2, 2008, the disclosure of which is expressly incorporated by reference herein in its entirety. Further, this application claims priority under 35 U.S.C. §119 and §365 of German Application No. 10 2007 014 520.0 filed Mar. 27, 2007.

BACKGROUND OF THE INVENTION

1. Field of the Invention

The application relates to a photoacoustic detector that has a high level of selectivity for measuring gases.

2. Background Description

Different types of detectors/sensors and analyzers can be used to measure and monitor the concentration of gaseous, air-contaminating substances in the air or impurities in process gases. An important family of gas sensors uses the selective absorption of light by the gas molecules.

Because the absorption spectrum is a very characteristic property of a molecule, absorption spectra or well selected absorption lines can be used to differentiate different contaminants or impurities, which are normally present in a gas.

The absorption of light in a gas can be measured in various ways. One method uses the so-called photoacoustic effect, the production of sound through light absorption. It is known that a photoacoustic signal can be produced only if the absorbed light energy is not constant, but changes from time to time. As a result, only modulated or pulsed light can produce a photoacoustic signal.

In photoacoustics, the intensity of a light beam, normally a laser beam, is periodically modulated either through a rotating chopper blade or the electronic driver unit of a laser source or light source. A further possibility is the modulation of the absorption in that, for example, the wavelength of a laser beam is periodically adjusted by a sharp absorption line of the molecule, which is to be detected (wavelength modulation). In this case, the light output of the light source, for example of the laser, remains constant, but the absorbed portion relevant for the photoacoustic measurement changes periodically. A third possibility is the use of a periodic pulse sequence of a pulsed laser.

Photoacoustic gas sensors use almost exclusively lasers as light sources. Previously, line-adjustable gas lasers such as $CO_2$ lasers or CO lasers were used, nowadays mainly diode lasers, quantum cascade lasers or adjustable non-linear laser sources are used. However, these devices are expensive. Although the photoacoustic detector is also simple and cheap per se, however, due to the price of the laser source, which accounts for between 80% and 90% of the total cost, these devices are suitable only for applications in which their outstanding capacity is also truly required.

Less expensive photoacoustic gas analyzers or gas monitoring devices use a broadband infrared source (incandescent lamp, infrared emitter, etc.). Because the light from these sources is absorbed by almost all molecules, it is very difficult to differentiate the species that are present in the air being monitored or in a gas being monitored. In order to improve the selectivity of these devices, in addition further spectrally selective elements must be used. Two examples of photoacoustic instruments that use broadband light sources and non-dispersive optical absorption are dealt with in detail in the two following sections.

A broadband light source is used in the case of gas analyzers made by INNOVA AirTech Instruments. In these commercially available instruments, a heated incandescent lamp is used as the light source. The incandescent lamp is localized in the first focus of an elliptical gold-coated mirror. A small photoacoustic cell is positioned such that the infrared light is focused in the center of the photoacoustic cell with the aid of the elliptical mirror through an infrared light-permeable window. The light is modulated by a rotating chopper wheel, and six different wavelength ranges can be selected by interference filters that are installed on a carousel wheel. This instrument has a sensitivity in the parts per million by volume (PPMV) range, however, its selectivity is limited because various other components possibly absorb in the wavelength range selected by the interference filter.

Another type of gas monitoring device (e.g., URAS made by ABB) uses a photoacoustic principle to detect the optical absorption. In this case, the light of a broadband infrared emitter is separated into two equal parts and modulated by a chopper. Then the two beams pass through two identical gas cells and reach two chambers of a differential detector. The two chambers are separated, but both are filled with the gas to be detected. Since the broadband light that reaches the chambers always includes the wavelengths that can be absorbed by the target molecules, photoacoustic signals are always produced in both chambers of the differential detector. If no light is absorbed in the gas cells on the way to the detector, the same light energy reaches both chambers, hence the photoacoustic signals in both chambers are the same and no differential signal appears as a result. In normal operation, however, the first gas cell (reference) is filled with a non-absorbing gas or gas mixture, while the second gas cell (sample) is filled with a gas to be monitored, for example, air. A portion of the light is absorbed in the sample cell, thus less light energy reaches the second chamber of the differential detector than the first chamber. For this reason, unequal photoacoustic signals are observed. The difference signal is greater if more light is absorbed in the sample cell. This instrument can be used as a monitoring device for the molecule that fills the differential detector. Its sensitivity is limited, however, because, in the case of a weak absorption in the sample cell, the difference signal in the detector is low. The limit of detection is thus determined by the offset of the infrared intensity and the fluctuations thereof on the two light paths.

A device is known from WO 2005/093390 A1 in which the radiation of a pulsed light source is alternately guided through a measuring cell A and a reference cell B into a photoacoustic measuring cell C. The absorption in the cell B is largely known, because a known gas with a known concentration is located there. Measuring cell A and reference cell B have an identical structure and differ only with regard to the gas contained. The difference of the photoacoustic signal, which is generated after passage of the radiation through cell A and cell B into the cell C, is a measure of the absorption in the cell A. Thus, inferences can be drawn about the type and concentration of an analyte in the cell A.

A similar structure is known from GB 2 358 245. This case also provides for radiation to be directed through a measuring cell and a reference cell and the quantity of the radiation transmitted to be determined photoacoustically in a further cell. As a result, the difference of the radiation directed through measuring cell and reference cell and thus the concentration of an analyte in the reference cell can be determined.

SUMMARY OF THE INVENTION

The aim of the present invention is therefore to overcome the disadvantages of the prior art and to provide a photoacoustic detector that renders possible a high selectivity even when broadband light sources, thus light sources that are available at low cost, are used. Similarly, an aim of the invention is to provide a corresponding measuring method. The aims are attained by the features of the independent claims. Advantageous further developments are found in the dependent claims. It was recognized that a photoacoustic detector is to be provided having the following structure:

Two light sources or one light source with a beam splitter for providing light of the same intensity and same spectral distribution are present. Furthermore, a first beam path allocated to the first light source and a second beam path allocated to the second light source are to be provided. It is to be guaranteed thereby that a different absorption of light can occur in the first and second beam paths in at least one selected wavelength range. Finally, the present invention includes a mechanism for alternately guiding light from the first and from the second beam path into a photoacoustic measuring cell.

In this manner it is achieved that in the selected wavelength ranges, in which there is a different absorption of the light in the first beam path and in the second beam path, the intensity of the light reaching the measuring cell changes temporally. If the light in the selected wavelength ranges is absorbed in the measuring cell, a photoacoustic signal is generated in the measuring cell. The photoacoustic signal is generated only in the case of a temporal change of the intensity of the incident light. Only then does heating take place through the absorption, which heating leads to expansions and sound waves caused therefrom. If the intensity remains constant, a continuous supply of heat occurs. However, a stationary state forms relatively quickly, in which heat supplied through the absorption of the light is dissipated uniformly and a constant temperature forms in the photoacoustic measuring cell. In this case, heating and expansions, which produce expansion waves, no longer occur. An absorption of the light in the wavelength ranges in which the same absorption exists in the first and in the second beam path, also does not produce a photoacoustic signal according to the aforementioned considerations. What is indeed important thereby is that the first and the second light source actually provide light with sufficiently identical intensity and identical spectral distribution of the intensity. Negligible differences in the intensity and/or in the spectral distribution can be accepted as long as they do not produce a no-longer-acceptable photoacoustic background signal also from the wavelength ranges in which the same absorption exists in the two beam paths. Furthermore, it is significant that the mechanisms that are designed to alternately supply light from the first and from the second beam path into the photoacoustic measuring cell, are structured such that the change from the first beam path to the second beam path takes place respectively so uniformly that, with the same intensity and spectral distribution in the first and in the second beam path, a constant light intensity that does not change temporally is supplied to the photoacoustic measuring cell. The change from the first to the second beam path takes place continuously in this process. To the degree to which the intensity decreases in the first beam path, the intensity in the second beam path simultaneously increases. On the other hand it holds that slight fluctuations of the light intensity can be accepted if they do not produce a photoacoustic signal that is no longer acceptable. The advantage of this structure as compared to the known structure, which directs light from two beam paths to two measuring cells and measures the difference signal, is that only absorption in the wavelength range in which the absorption is different in the two beam paths, contributes to the signal. This results in a tendency to higher measuring accuracy than with a structure in which wide wavelength ranges contribute to the signal and then the difference is taken, as provided with the Uras device made by ABB. The intensity of the two radiation sources is thereby constant such that its temporal change cannot generate a photoacoustic signal that would distort the measurement. A slight change in the intensity of a light source could be accepted if this results in only a photoacoustic signal that does not distort the measurement.

One possibility of providing light of the same intensity and the same spectral distribution in the first and the second light source is to form the first and the second light source by a common light source, the radiation of which can be split in a beam splitter. Beam splitters are available with which a beam can be split with satisfactory precision into two identical partial beams.

A further possibility that is definitely cost-effective for providing light of the same intensity and same spectral distribution in the first and second light source is to provide identical light emitters, in particular identical infrared emitters.

As explained, a photoacoustic signal should not be produced in the case of the same absorption in both beam paths. Because it is easy to realize an identical absorption in both beam paths, a test measurement with the same absorption can be carried out, in which no photoacoustic signal should be discernible. If a photoacoustic signal is nevertheless discernible thereby, this indicates that the intensity and spectral distribution of the two light sources is different or the transition from one beam path to the next one does not occur uniformly enough. Remedial action can be taken accordingly.

If a reference cell is positioned in the first beam path and an absorption cell is positioned in the second beam path, which absorption cell absorbs in selected wavelength ranges, a different absorption can take place in a simple and reproducible manner in the different beam paths. It is thereby beneficial if the absorption cell is easily removable in order to be able to insert different absorption cells according to requirements. The selection of the beam path in which the absorption cell is positioned and of the beam path in which the reference cell is positioned is arbitrary. The important factor is that the absorption cell is located in one beam path and the reference cell is located in the other.

In order to achieve the highest possible acoustic signal, and thus the most sensitive measurement possible, it is expedient if the absorption cell contains the same substance, the concentration of which is to be measured in the photoacoustic measuring cell.

As a result, the absorption is different in precisely the wavelength ranges that produce in the photoacoustic measuring cell a photoacoustic signal that can be attributed to the presence of the substance being tested.

The substance being tested usually relates to gas constituents, the concentration of which in a gas is to be measured. This is the case because here photoacoustic measurements can be performed especially well, since the expansion in the case of heat and thus the photoacoustic signal is particular high in gases. In principle, the photoacoustic measuring cell in the present case can also be embodied for detection in gases or liquid.

A further improvement is produced if the reference cell in the non-selected wavelength ranges has the same absorption as the absorption cell. In practice, it may be very difficult to find an absorption cell which absorbs only in the wavelength ranges in which a different absorption is desired. In fact every absorption cell has windows; furthermore, the substances whose absorption capacity is desired are as a rule in a carrier gas. This produces an absorption also in the wavelength ranges, in which the same absorption is desired in both beam paths. This can be equalized by a reference cell which has the same adsorption in the non-selected wavelength ranges as the absorption cell. This can be realized practically by selecting an absorption cell which contains a carrier gas with the absorbing substance and an absorption cell which contains the carrier gas without the absorbing substance.

In order be able to use the photoacoustic detector for a greatest number of different wavelength ranges, and thus for the greatest number of substances, it is expedient that different absorption cells and/or reference cells are present, which can be positioned in the beam path. As a result, different substances, which absorb well in different wavelength ranges, can be measured. In addition, it is possible to measure the photoacoustic signal in the case of different wavelength ranges, i.e., in the case of different wavelength ranges in which a different absorption exists in the first and in the second beam path. This can be very advantageous for increasing the selectivity, i.e., the determination of which substance or which mixture of substances is present in the measuring cell.

A simple possibility for implementing the aforementioned improvement is to arrange the different absorption cells and/or reference cells in the manner of a carousel on a circular path, and to be able to rotate a desired absorption cell and/or reference cell into the first and/or second beam path. As a result, with a simple structure, many wavelength ranges can be selected in which a different absorption exists in the first and in the second beam path.

One mechanism for alternately supplying light from the different beam paths to the photoacoustic measuring cell, is a rotatable, in particular polygonal, mirror. This can be structured in such a way and rotated in such a way that it is possible to switch from one beam path to a second beam path in a very short time. Rotating mirrors of this type are used in laser printers and are thus available cost-effectively as reliable mass-produced articles. A further mechanism is an oscillating mirror with a specific oscillation frequency. Mirrors of this type are installed in laser scanners and are thus also available cost-effectively as a mass-produced article. Despite the aforementioned measures, the problem can remain that a signal is also generated in the photoacoustic measuring cell, which is not attributable to the substance being tested, but to an absorption, for instance, in the windows of the photoacoustic measuring cell. To prevent this from leading to a distortion of the measurement, it is possible to provide a further photoacoustic measuring cell as a comparison measuring cell, into which light can be directed as in the photoacoustic measuring cell and which is structured just like the photoacoustic measuring cell. It is understood thereby that it must be assured that light of the same spectral intensity and same spectral distribution actually reaches the measuring cell and the comparison measuring cell. The difference of the signals obtained from the measuring cell and the comparison measuring cell is clearly attributable to the substance being tested, as long as the measuring cell and the reference measuring cell differ only in terms of the presence of the substance. If the substance to be tested is present in a carrier gas, it must be ensured that the same carrier gas without the substance to be tested is present in the comparison measuring cell.

BRIEF DESCRIPTION OF THE DRAWING

Without restricting the universality, the invention is described in greater detail below on the basis of an exemplary embodiment. In this case.

DETAILED DESCRIPTION OF THE INVENTION

Figure 1:
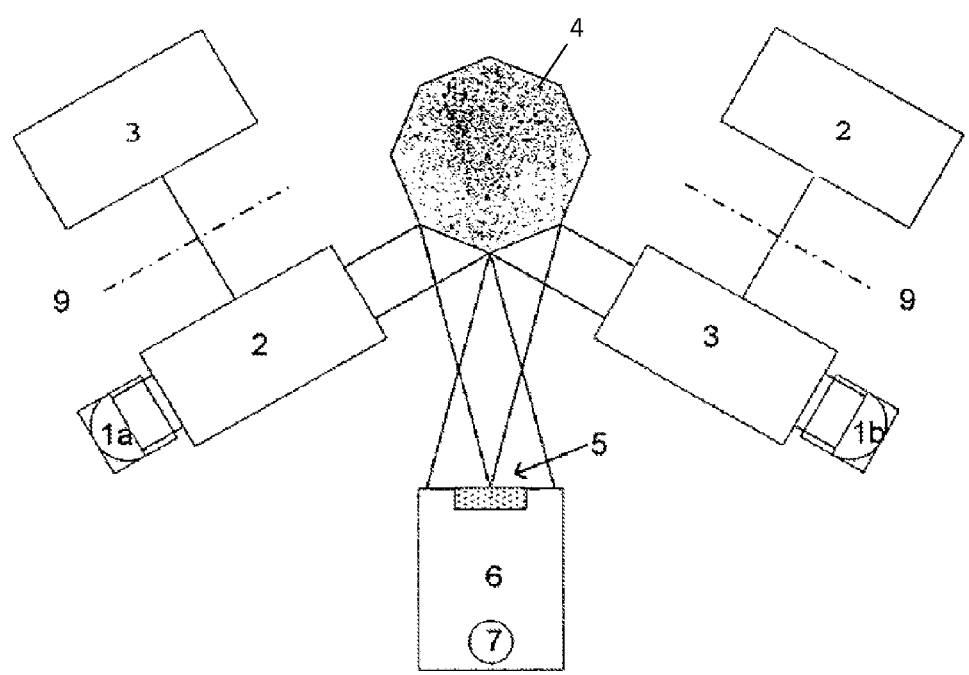
FIG. 1 shows a possible structure of the photoacoustic detector.

Two identical miniature infrared emitters $1a$, $1b$, which are equipped with parabolic mirrors, emit parallel infrared beams. The infrared beam from the emitter $1a$ goes through the reference cell 2 filled with dry synthetic air, while the beam from the other infrared emitter $1b$ goes through the absorption cell 3, which is filled with a mixture of dry synthetic air and a target gas, the molecules of which absorb a portion of the infrared light. The concentration of the target gas in the absorption cell 3 is selected such that at least 95% of the infrared light is absorbed at the strongest absorption line of the target gas.

The infrared beams are reflected by a polygonal mirror 4 alternatively to the infrared-transmitting window 5 and reach the photoacoustic cell 6, which is equipped with a measuring microphone 7. The intensity of the infrared light in the photoacoustic cell is constant in the case of wavelengths in which no absorption takes place in the absorption cell 3, but it is modulated in the case of wavelengths in which the target gas absorbs the light in the absorption cell 3. Because a photoacoustic signal can be generated only through the modulated portion of the light, only those components of the gas in the photoacoustic cell 6 can produce photoacoustic signals, which components, in the case of the absorption wavelengths of the target gas, also themselves absorb in the reference cell 2. Thus, the target gas located in the absorption cell 3 must also absorb in the ranges in which the gas being detected in the photoacoustic cell 6 absorbs. The photoacoustic signal is naturally greatest when the same gas is present in the absorption cell 3 and in the photoacoustic cell 6.

Different gases can be detected by using additional absorption cells 3, which are filled with gas mixtures, which contain different target molecules. In the system depicted in FIG. 1, reference cells 2 and absorption cells 3 are mounted on two rotatable carousel wheels 9. It is possible to mount six reference cells or absorption cells 2, 3, on each carousel wheel 9, thus there is space for one reference cell 2 and five absorption cells 3 on each carousel wheel 9. In this way, ten different gases can be detected with this instrument. The number of 6 reference cells or absorption cells on each carousel wheel 9 is selected, because this makes a relatively high number of cells possible with a comparatively low space requirement. Of course, a higher or lower number would also be possible.

The two reference cells 2 are required to minimize the photoacoustic interference signal, which occurs due to the slight changes in the light energy in the photoacoustic cell 6. The periodic change of the light energy due to the imbalance of the two channels can produce an external noise signal that can be attributed to the light absorption in the infrared-transmitting window 5. If both carousel wheels are rotated such that the reference cells 2 are positioned in both beam paths, and both reference cells 2 as well as the photoacoustic cell 6 are filled with the non-absorbing reference mixture, the external noise signal can be minimized or eliminated by changing the alignment of the infrared beams and/or the supply voltage of the infrared emitters 1a, 1b.

The photoacoustic gas sensor can be calibrated in that the photoacoustic cell 6 is filled with known gas mixtures of different target gases. The cross-sensitivities of the instrument can be determined in that the photoacoustic signal is measured in the photoacoustic cell 6, which is filled with a mixture from the $n^{th}$ target gas, if the other nine absorption cells 3 filled with the target gas are used for modulation.

Figure 2:
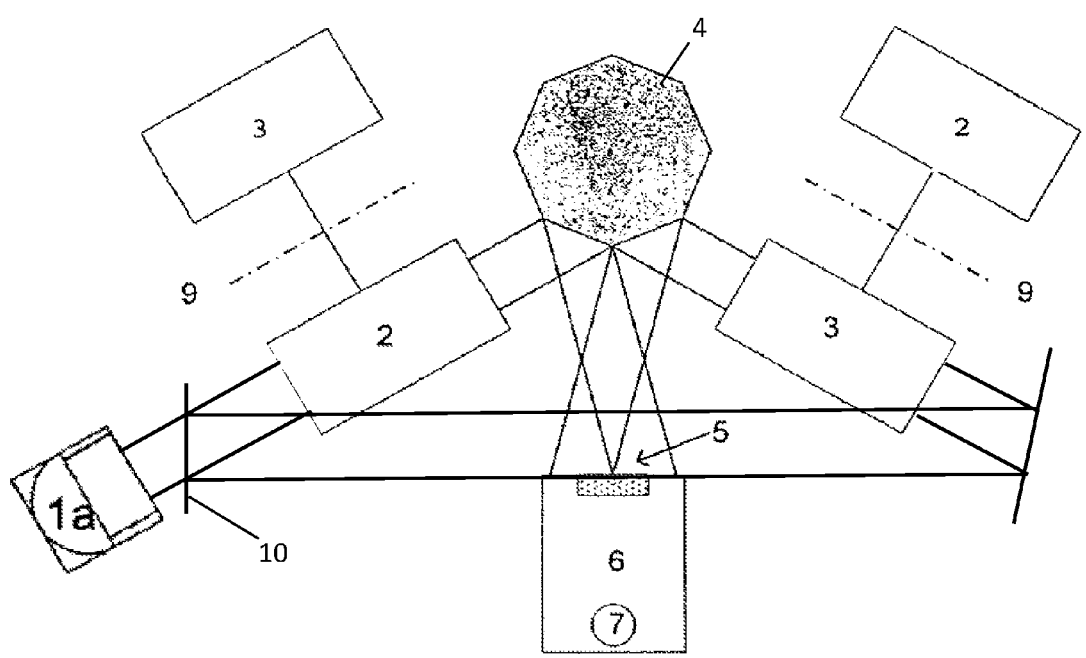
FIG. 2 shows a possible structure of another photoacoustic detector with a single light source.

FIG. 2 illustrates one possibility of providing light of the same intensity and the same spectral distribution in the first and the second light source is to form the first and the second light source by a common light source 1a, the radiation of which can be split in a beam splitter 10. Beam splitters are available with which a beam can be split with satisfactory precision into two identical partial beams.

Figure 3:
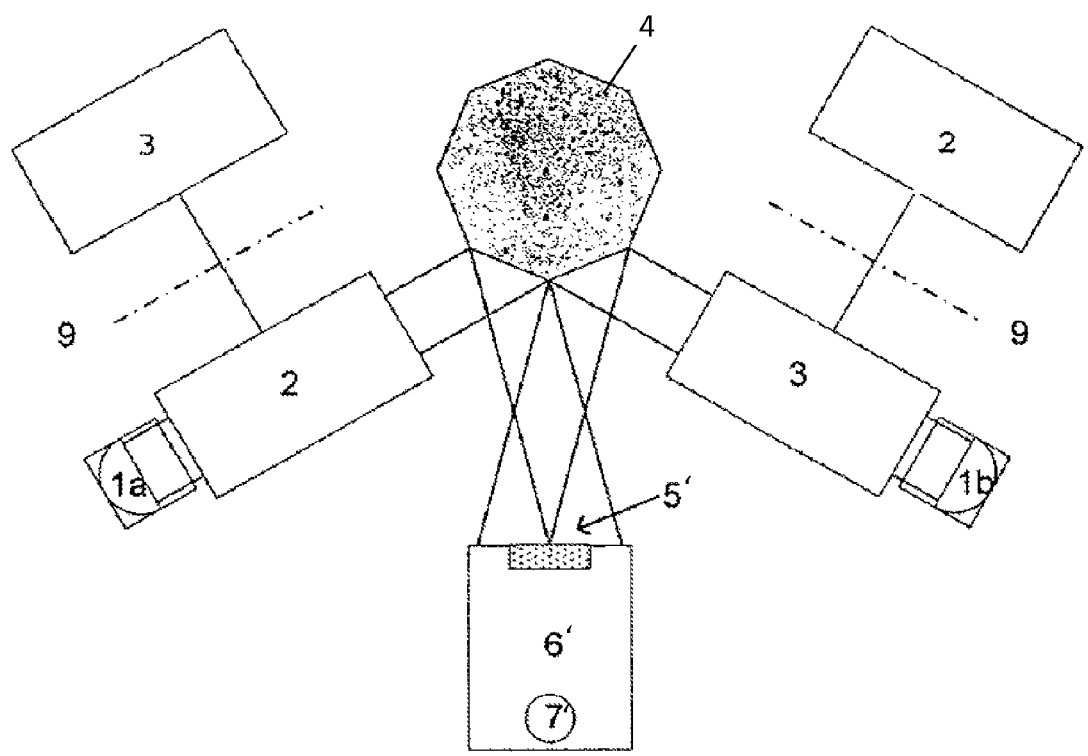
FIG. 3 shows a possible structure of another photoacoustic detector with a photoacoustic comparison measuring.

FIG. 3 illustrates a further photoacoustic measuring cell as a comparison measuring cell 6', into which light can be directed as in the photoacoustic measuring cell (which may be arranged directly below the comparison measuring cell 6', and is thus not shown in FIG. 3) and which is structured just like the photoacoustic measuring cell 6 to include an infrared-transmitting window 5' and measuring microphone 7'.

LIST OF REFERENCE NUMBERS 1a, 1b: Miniature infrared emitter
2: Reference cell
3: Absorption cell
4: Polygonal mirror
5: Infrared-transmitting window
6: Photoacoustic cell
7: Measuring microphone
9: Carousel wheel

The invention claimed is:

1. A photoacoustic detector for providing a measurement, comprising:
a first light source and a second light source each configured to provide light of a same intensity while retaining a same spectral distribution;
a first beam path allocated to the first light source;
at least one second beam path allocated to the second light source, wherein a different absorption of light occurs in the first path and the second beam path in at least one selected wavelength range;
a photoacoustic measuring cell; and
a mechanism for alternately guiding light from the first beam path and from the second beam path into the photoacoustic measuring cell,
wherein when alternately guiding light from the first beam path and from the second beam path into the photoacoustic measuring cell, the same intensity of the first light source and the second light source prevents generation of a photoacoustic signal due to light source intensity variation that distorts the measurement,
the photoacoustic detector further comprising at least one absorption cell configured to absorb in selected wavelength ranges and positionable in the first beam path or the second beam path.

2. The photoacoustic detector of claim 1, further comprising a beam splitter, wherein the first light source and the second light source comprise a common light source whose radiation is split with the beam splitter.

3. The photoacoustic detector of claim 1, wherein the first light source and the second light source comprise identical light emitters.

4. The photoacoustic detector of claim 3, wherein the identical light emitters comprise infrared emitters.

5. The photoacoustic detector of claim 1, wherein:
the absorption cell contains a concentration of a substance;
the photoacoustic measuring cell contains the substance; and
the photoacoustic measuring cell is configured to measure the concentration.

6. The photoacoustic detector of claim 1, further comprising at least one reference cell which has a same absorption as the absorption cell in wavelength ranges other than the selected wavelength ranges, and which is positionable in the first beam path or the second beam path.

7. The photoacoustic detector of claim 6, wherein at least one of:
the at least one absorption cell comprises a plurality of absorption cells positionable in the first beam path or the second beam path; and
the at least one reference cell comprises a plurality of reference cells positionable in the first beam path or the second beam path.

8. The photoacoustic detector of claim 6, further comprising at least one carousel having a circular path, wherein at least one of the plurality of absorption cells and the plurality of reference cells are arranged on the at least one carousel, such that at least one of a desired absorption cell a desired reference cell is rotatable via the at least one carousel into at least one of the first beam path and the second beam path.

9. The photoacoustic detector of claim 1, wherein the mechanism for alternately guiding light into the photoacoustic measuring cell comprises one of an oscillating or a rotatable mirror.

10. The photoacoustic detector of claim 1, wherein the photoacoustic measuring cell further comprises a window, and wherein the mechanism for alternately guiding the light from the first beam path and from the second beam path into the photoacoustic measuring cell is structured and arranged to alternately guide light from the first beam path and from the second beam path through the window and into the photoacoustic measuring cell.

11. A photoacoustic detector for providing a measurement, comprising
a first light source and a second light source each configured to provide light of a same intensity while retaining a same spectral distribution;
a first beam path allocated to the first light source;
at least one second beam path allocated to the second light source, wherein a different absorption of light occurs in the first path and the second beam path in at least one selected wavelength range;
a photoacoustic measuring cell; and
a mechanism for alternately guiding light from the first beam path and from the second beam path into the photoacoustic measuring cell,
wherein when alternately guiding light from the first beam path and from the second beam path into the photoacoustic measuring cell, the same intensity of the first light source and the second light source prevents generation of a photoacoustic signal due to light source intensity variation that distorts the measurement,
wherein the mechanism for alternately guiding light into the photoacoustic measuring cell comprises one of an oscillating or a rotatable mirror, and
wherein the mirror comprises a polygonal mirror.

12. A photoacoustic detector for providing a measurement, comprising
- a first light source and a second light source each configured to provide light of a same intensity while retaining a same spectral distribution;
- a first beam path allocated to the first light source;
- at least one second beam path allocated to the second light source, wherein a different absorption of light occurs in the first path and the second beam path in at least one selected wavelength range;
- a photoacoustic measuring cell; and
- a mechanism for alternately guiding light from the first beam path and from the second beam path into the photoacoustic measuring cell,
- wherein when alternately guiding light from the first beam path and from the second beam path into the photoacoustic measuring cell, the same intensity of the first light source and the second light source prevents generation of a photoacoustic signal due to light source intensity variation that distorts the measurement,
- the photoacoustic detector further comprising a photoacoustic comparison measuring cell configured and arranged to receive light from at least one of the first light source and the second light source.

13. The photoacoustic detector of claim 12, wherein the photoacoustic comparison measuring cell comprises a corresponding element for each element of the photoacoustic measuring cell.

14. A method for determining a concentration measurement of an analyte photoacoustically in a photoacoustic measuring cell of a photoacoustic detector, the photoacoustic detector comprising at least one absorption cell configured to absorb in selected wavelength ranges and positionable in the first beam path or the second beam path, the method comprising:
- alternately supplying light from first light source through a first beam path and from a second light source through a second beam path into the photoacoustic measuring cell to determine the measurement;
- wherein the supplied light in the first beam path and in the second beam path:
    - is of a same intensity and retains a same spectral distribution, and
    - is absorbed at different strengths in selected wavelength ranges,
    - wherein in one of the beam paths the light is absorbed by the at least one absorption cell,
- and wherein when alternately supplying light from first light source through a first beam path and from a second light source through a second beam path into the photoacoustic measuring cell, the same intensity of the supplied light prevents generation of a photoacoustic signal due to light source intensity variation that distorts the measurement.

15. The method of claim 14, wherein the photoacoustic measuring cell further comprises a window, and wherein the alternately supplying the light from first light source through the first beam path and from the second light source through the second beam path into the photoacoustic measuring cell comprises alternately supplying the light from first light source through the first beam path and from the second light source through the second beam through the window and into the photoacoustic measuring cell.

* * * * *